(12) United States Patent
Roenneburg et al.

(10) Patent No.: US 7,361,269 B2
(45) Date of Patent: Apr. 22, 2008

(54) FRACTION COLLECTOR WITH ADJUSTABLE TRAY

(75) Inventors: Lucas D. Roenneburg, Albany, WI (US); Jeffrey L. Acker, Middleton, WI (US)

(73) Assignee: Gilson, Inc., Middleton, WI (US)

( * ) Notice: Subject to any disclaimer, the term of this patent is extended or adjusted under 35 U.S.C. 154(b) by 336 days.

(21) Appl. No.: 11/221,589

(22) Filed: Sep. 8, 2005

(65) Prior Publication Data

US 2006/0054544 A1 Mar. 16, 2006

Related U.S. Application Data

(60) Provisional application No. 60/609,105, filed on Sep. 10, 2004.

(51) Int. Cl.
*B01D 15/08* (2006.01)
(52) U.S. Cl. ............... 210/198.2; 210/656; 210/659; 422/63; 422/70; 422/100
(58) Field of Classification Search ............... 210/656, 210/659, 198.2; 422/63, 70, 100
See application file for complete search history.

(56) References Cited

U.S. PATENT DOCUMENTS

| | | | |
|---|---|---|---|
| 3,151,639 A | 10/1964 | Allington | |
| 3,168,124 A | 2/1965 | Lenkey | |
| 3,268,117 A * | 8/1966 | Lenkey et al. ................. | 222/14 |
| 3,418,084 A | 12/1968 | Allington | |
| 3,943,983 A | 3/1976 | Gelfand | |
| 4,077,444 A | 3/1978 | Gilson | |
| 4,147,250 A | 4/1979 | Schulz | |
| 4,166,094 A | 8/1979 | Froehlich et al. | |
| 4,166,483 A | 9/1979 | Nordlund | |
| 4,356,909 A | 11/1982 | November et al. | |
| 4,422,151 A | 12/1983 | Gilson | |
| 4,766,082 A * | 8/1988 | Marteau D'Autry | ........ 436/178 |
| 4,862,932 A | 9/1989 | Feinstein et al. | |
| 5,417,123 A * | 5/1995 | Marteau D'Autry | ..... 73/864.25 |
| 5,595,664 A * | 1/1997 | Sanford et al. | ............. 210/656 |
| 6,133,045 A * | 10/2000 | Johnson et al. | ............. 436/177 |
| 6,197,198 B1 * | 3/2001 | Messinger et al. | .......... 210/656 |
| 6,355,164 B1 | 3/2002 | Wendell et al. | |
| 6,450,218 B1 | 9/2002 | Andersson | |
| 6,551,464 B1 | 4/2003 | Kimel | |
| 7,138,050 B2 * | 11/2006 | Maruyama et al. | ...... 210/198.2 |

OTHER PUBLICATIONS

Page print of http://www.isco.com/aspscripts/products2.asp?PL=10160&image=Chromatography2.jpg website dated Oct. 8, 2003.
Page print of http://www1.dionex.com/en-us/hplc_hardware/ins_dxpm6919.html website dated Apr. 2, 2004.

(Continued)

*Primary Examiner*—Ernest G. Therkorn
(74) *Attorney, Agent, or Firm*—Foley & Lardner LLP (57) ABSTRACT

A fraction collector comprising a movable tray is provided. The movable tray may be attached to the fraction collector support system in a variety of ways and adjusted without adjusting the parts of the fraction collector support system. The moveable tray may be stably attached to the fraction collector support system by either fixed or removable pegs, as well as by channels.

14 Claims, 6 Drawing Sheets

OTHER PUBLICATIONS

"FOXY 200 Fraction Collector" brochure, pp. 6-9, undated.
"IFC Fraction Collector" brochure, LEAP Technologies, Carrboro, NC, undated.
"Preparative Fraction Collector" brochure, GERSTEL Global Analytical Solutions, undated.
Page Print from http://www.varianinc.com/cgi-bin/advprint/print.cgi?cid=IOPJPPLFP website on Apr. 2, 2004 for Varian, Inc.; HPLC Fraction Collectors, pp. 1-3, Apr. 2, 2004.
"Flexible fraction Collection from µg to gram quantities" brochure, Agilent 1100 Series Modules and Systems for LC and LC/MS, Agilent Technologies, Jun. 1, 2002.
"FC I Fraction Collector" brochure, Lab Alliance, Rev. 3, Feb. 14, 2002.
"FRC-10A Fraction Collector for Shimadzu HPLC System" brochure, Shimadzu, Japan, undated.
"Fraction Collector SuperFrac™" User Manual, Amersham Biosciences, undated.

* cited by examiner

FRACTION COLLECTOR WITH ADJUSTABLE TRAY

REFERENCE TO RELATED APPLICATION

This application claims the benefit of provisional application No. 60/609,105, filed Sep. 10, 2004 the disclosure of which is incorporated herein by reference.

FIELD OF THE INVENTION

The present invention is directed to a collection apparatus and methods for use of the collection apparatus. The present invention relates to liquid handling devices and more particularly to fraction collectors. The devices of the present invention may be used for chromatographic separations, sample purifications, and more particularly, for high throughput purification of samples from a chemical library.

BACKGROUND

Fraction collectors are well-known devices intended for collecting liquid samples originating from slow-flowing sources having variable liquid compositions. Fraction collectors are typically used in chromatographic separations such as high performance liquid chromatography (HPLC), gas chromatography (GC), supercritical fluid chromatography (SFC), column chromatography, and liquid-liquid separations, and for the collection of distillates from various distillation processes. The size of each individual sample or fraction dispensed by the fraction collector is determined by conventional measuring equipment such as a timer, a drop counter, a level sensing device, or by a variety of spectrophotometric methods. Fraction collectors typically sequentially align a dispensing head, carry a sample delivery conduit or tube over individual collection vessels part of an array of collection vessels, and deliver sample to collection vessels.

Fraction collectors may be broadly categorized into two groups. The first group includes fraction collectors in which a plurality of collection vessels are mounted on a generally circular turntable. These fraction collectors are commonly called "turntable collectors." The turntable collectors all generally operate to fill a plurality of collection vessels by the combination of a rotatably mounted turntable and a rotatably mounted arm carrying a dispensing head. The dispensing head is typically aligned over a single collection vessel, the liquid is dispensed into the collection vessel, and the turntable then rotates to align with another collection vessel. In turntable collectors, the plurality of collection vessels are typically arranged in a concentric circular or spiral pattern. In order to manipulate the dispensing head over collection vessels in different circles of a concentric pattern or with an expanding or contracting spiral pattern, the rotatably mounted arm moves to align the dispensing head with each of the individual collection vessels in the arrangement.

The second group of fraction collectors includes collectors with the collection vessels arranged in a grid pattern on a stationary stage, and a dispensing head manipulated in either a 2-dimensional plane or in all three dimensions to selectively dispense liquid into the individual collection vessels. Fraction collectors in the second group are commonly called "X-Y collectors."

The two groups of fraction collectors each have distinct advantages. For example, when handling a large number of liquid collection vessels, fraction collectors with rectangular grid patterns more effectively use bench space. X-Y collectors are also better suited to handling large scale collection vessels than are the rotatably mounted turntables. Furthermore, X-Y collectors may be adapted to popular standardized receptacle plates, such as microtiter plates, or other standard or custom arrangements. In contrast, turntable-type fraction collectors may be more advantageous when used in high resolution liquid chromatography as they require shorter attachment tubing between the slow-flowing source and the dispensing head, thus limiting diffusional re-mixing of the separated components within the liquid flow and resulting in better separation.

Both X-Y and turntable fraction collectors must be adjusted to fit the collection vessels used for sample collection, which commonly come in various sizes. Generally, vertical adjustment of the fraction collector has typically been done by either manual adjustment of the legs or incorporation of a vertical adjustment (Z-axis) of the dispensing head. The first method, utilized in some X-Y collectors, allows for manual adjustment of the height of the dispensing head by removing the legs of the base of the fraction collector and putting on longer or shorter legs as desired. However, while this method can be effective, if the legs of the base are adjusted manually, the racks containing the collection vessels need to be removed during adjustment, as the legs can only be adjusted individually. Furthermore, it is difficult to balance the collection bed during the adjustment, creating the opportunity for spillage to occur. Moreover, manual adjustment requires realignment of the dispensing head with the collection vessels and collection bed, introducing additional steps that could damage the fraction collection apparatus. As fraction collectors have become more advanced, the tolerances have become tighter, and therefore manual adjustment of the dispensing head assembly threatens to damage some of the fragile electrical parts.

In addition, manual vertical dispensing head adjustment may knock the dispensing head out of horizontal alignment, causing the liquid fractions to miss the sample collection vessels. This can result in lost time in cleaning up the liquid, damage to the instrument, or present a hazardous environment for the operator, depending on the contents of the liquid. Furthermore, when a dispensing assembly is knocked out of alignment, the precision alignment procedures required to realign the assembly can be very time consuming.

Incorporation of a vertical adjustment (Z-axis) axis into the dispensing head is known in the art. However, fraction collectors with a Z-axis require complex mechanics, and sometimes software, in order to get the dispensing head to move reliably and precisely in all three directions. These complex mechanics often add both size and cost. Furthermore, because collection vessels used in a single fraction collection run are commonly of uniform size, a dispensing head that moves in a vertical direction is often unnecessary.

Regardless of whether the fraction collector is an X-Y collector or a turntable collector, it is of primary importance in the design that the mechanism for aligning the dispensing head and collection vessels be as simple and as sturdy as possible, while being reliably capable of precisely positioning the dispensing head over sequential collection vessel. Although many fraction collectors known in the art can reliably and precisely position the dispensing head over a sequential collection vessel, many are quite complex and therefore not only expensive but difficult to adjust and maintain. In particular, known fraction collector arrangements may include dispensing head adjustment mechanisms that are extremely complicated and delicate.

Therefore, a need exists for a fraction collector that reliably and precisely aligns a dispensing head and collection vessel without adding significant cost or fragility.

SUMMARY OF THE INVENTION

This invention relates to a new device for adjusting the distance between the dispensing head and the collection vessel on a fraction collector. More specifically, this invention relates to a bed on a fraction collector that can be adjusted without adjusting the legs of the fraction collector. Because the bed of the fraction collector can be adjusted, there is no need for a Z-axis on the dispensing head.

In one embodiment, the invention provides for a fraction collector that includes a support system, a carriage movably supported by the support system, an extension arm attached to the carriage, a dispensing head moveably attached to the extension arm, wherein the dispensing head and carriage can move along the support system in a first plane, and a collection bed moveably connected to the support system wherein the collection bed may be moved in a second plane perpendicular to the first plane without adjusting the support system.

In certain embodiments, the invention may comprise a method for using the fraction collector by determining a proper displacement of the collection bed from the dispensing head, aligning the collection bed with the support system at the proper displacement, and stably attaching the collection bed to the support system.

In one embodiment of the present invention, the fraction collector includes a support system, a carriage including an extension arm with a dispensing head connected to the support system, wherein the dispensing head and carriage move together in a single plane, and a collection bed connected to the support system such that the collection bed is adjustable in a direction perpendicular to the single plane. In this embodiment, the support system for the fraction collector comprises left and right legs with leg bases and a front and top brace. Generally the support system supports both the carriage and the collection bed. In some embodiments, the single plane is an X-Y plane level with and parallel to a support surface such as a bench or table and the direction perpendicular to the single plain is the Z direction. Typically, the collection bed will be capable of holding collection vessels of various sizes and shapes with or without a system of racks.

In another aspect of the invention, the collection bed of the fraction collector is made of a tray having two side edges and front and rear edges. Attached to the collection bed are collection bed arms which extend to attach the collection bed to the support system. In one embodiment of the invention, the support system has a series of pegs in the right and left legs and the collection bed arms have anchor points spaced in a complementary fashion to the pegs in the legs of the support system. The collection bed may be vertically adjusted by raising or lowering the collection bed and locking the collection bed in place on the support system through the pegs and anchor points on the collection bed arm. In alternative embodiments, the anchor points on the collection bed may be slots or holes and the pegs in the legs may be fixed or removable.

In another embodiment, the collection bed may be vertically adjusted by raising or lowering the collection bed and locking the collection bed in place on the support system through a series of peg holes in the right and left legs, and anchor holes on the collection bed arms such that removable pegs may be inserted through the anchoring holes and into the peg holes to secure the collection bed in place.

In still another embodiment, the collection bed arms are angularly disposed from the tray of the collection bed by an angle, such that when the tray is tipped back the whole collection bed is vertically adjustable. In this and other related embodiments, the right and left legs of the support system may have grooves or notches for retaining the vertical adjustment of the collection bed. Furthermore, in certain embodiments, the rear edge of the collection bed tray may be shaped to fit into the grooves or notches, or the rear edge of the collection bed tray may have an attached complementary shape to the grooves or notches such that the complementary shape precisely fits into the groove or notch.

In yet another aspect of the invention, the right and left legs of the fraction collector support system may have exterior or interior channels capable of holding the collection bed at a level orientation when the collection bed arms are inserted into them.

Other embodiments of the invention may include a fraction collector for dispensing liquid from a dispensing head into collection vessels carried on a collection bed, the fraction collector includes a support system, a carriage including an extension arm with a dispensing head connected to the support system, wherein the dispensing head and carriage move together in a single plane, and a collection bed connected to the support system such that the collection bed is adjustable by way of lift movement.

In other contemplated embodiments of the invention, the collection bed may not be attached to the apparatus and instead may rest upon or fully integrate a stage that can be raised or lowered manually, via hydraulic methods, or with a motorized screw mechanism. In such embodiments, the collection bed needs will be reliably and precisely aligned with the dispensing head on the apparatus using markings on the fraction collector and collection bed, positioning lasers on the apparatus, and/or markings on both the fraction collector and support on which the fraction collector rests, such as a laboratory bench.

DETAILED DESCRIPTION OF THE PREFERRED EMBODIMENTS

Figure 1:
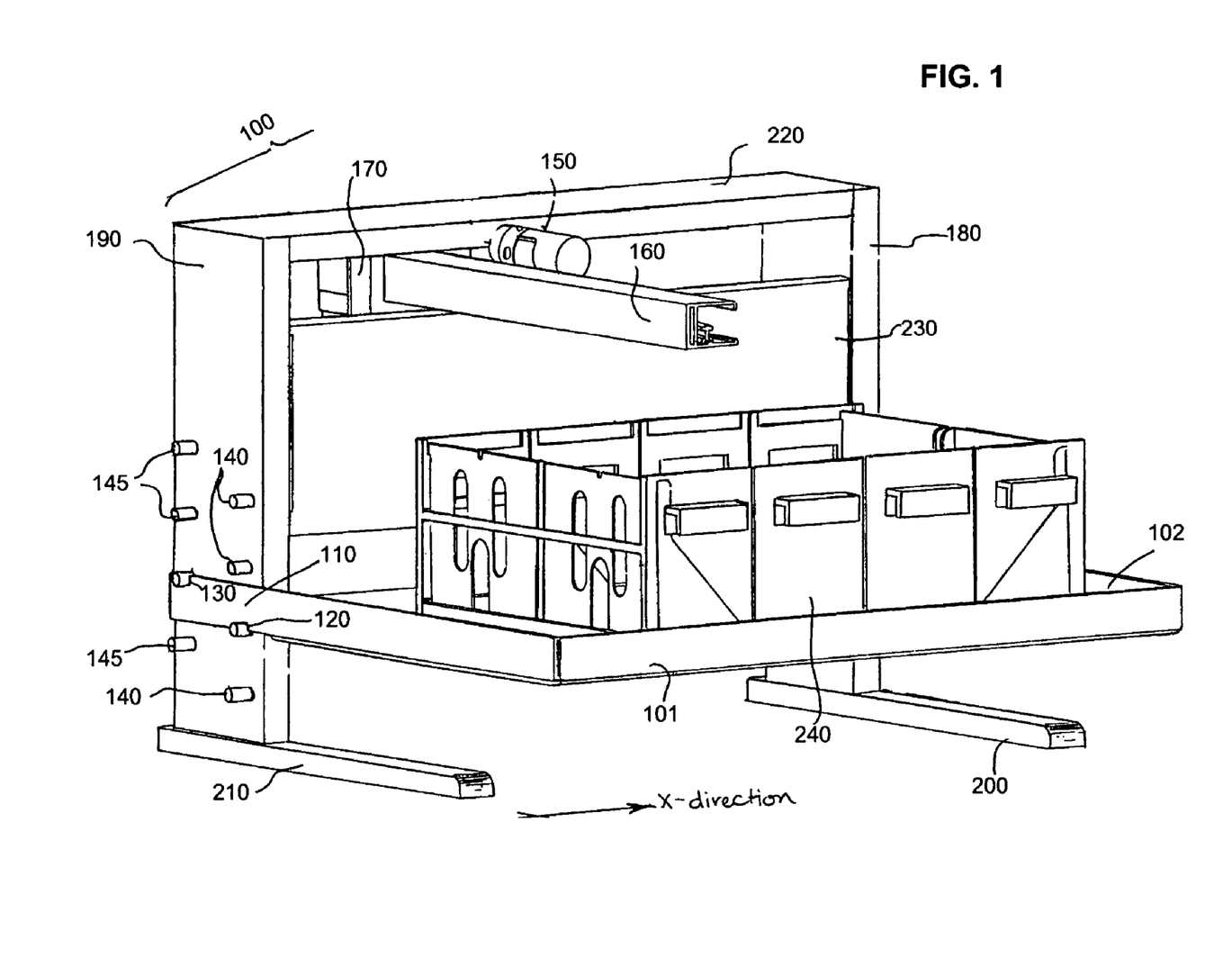
FIG. 1 is a perspective view of a fraction collector demonstrating the use of pegs on the legs of the fraction collector.

As illustrated by the embodiment of FIG. 1, the fraction collector device 100 comprises a vertically adjustable collection bed 101 in a given position under a dispensing head 150. As one of skill in the art will understand, this given position may be in any of a range of positions. As a non-limiting example, the given positions may be appropriate for racks containing collection vessels of known size. In other embodiments, the given position may be adjustable along a continuum allowing the use of custom collection vessels. The dispensing head 150 is moveably mounted on an extension arm 160 that is in turn moveably mounted on a carriage 170. In the embodiment demonstrated by FIG. 1, the dispensing head 150 is capable of movement along the extension arm 160 in a Y-direction, and the extension arm 160 is capable of movement in an X-direction. The skilled artisan understands that the X and Y directions are arbitrarily assigned and not meant to be limiting. Embodiments where the dispensing head 150 moves in the X-direction and the extension arm 160 moves in the Y-direction are anticipated.

The fraction collector 100, as shown in FIG. 1, is supported by a left leg 180, a left leg base 200, a right leg 190, and a right leg base 210. As will be understood by one skilled in the art, the bases of the legs may be any shape adequate to stabilize the legs. Although a certain shape of base is demonstrated in the figures, the base is not meant to be so limiting. The two legs are connected by a top brace 220 and a front brace 230. Although the embodiment of FIG. 1 demonstrates the top brace 220 and front brace 230 as permanently connecting the two legs, further embodiments anticipate the top brace 220 and the front brace 230 as removably connected to the two legs, such as through the use of screws. Additional embodiments contemplate the front brace extending to the support surface. In some embodiments, the legs, leg bases, and braces will form a support system for the fraction collector. In still other embodiments, it is contemplated that the support system will not include a front brace.

The carriage 170 is mounted behind the front brace 230 by one of a number of methods well known to those of ordinary skill in the art. The collection bed 101 has a tray area 102 where the racks 240 are situated, as shown, or where individual collection vessels may be arranged using a system other than the rack system. The collection bed 101 further has two collection bed arms 110, that extend from the tray area of the collection bed 101, and provide attachment of the collection bed to the left 180 and right leg 190. The collection bed arms 110 allow for vertical height adjustment of the collection bed 101.

Figure 2:
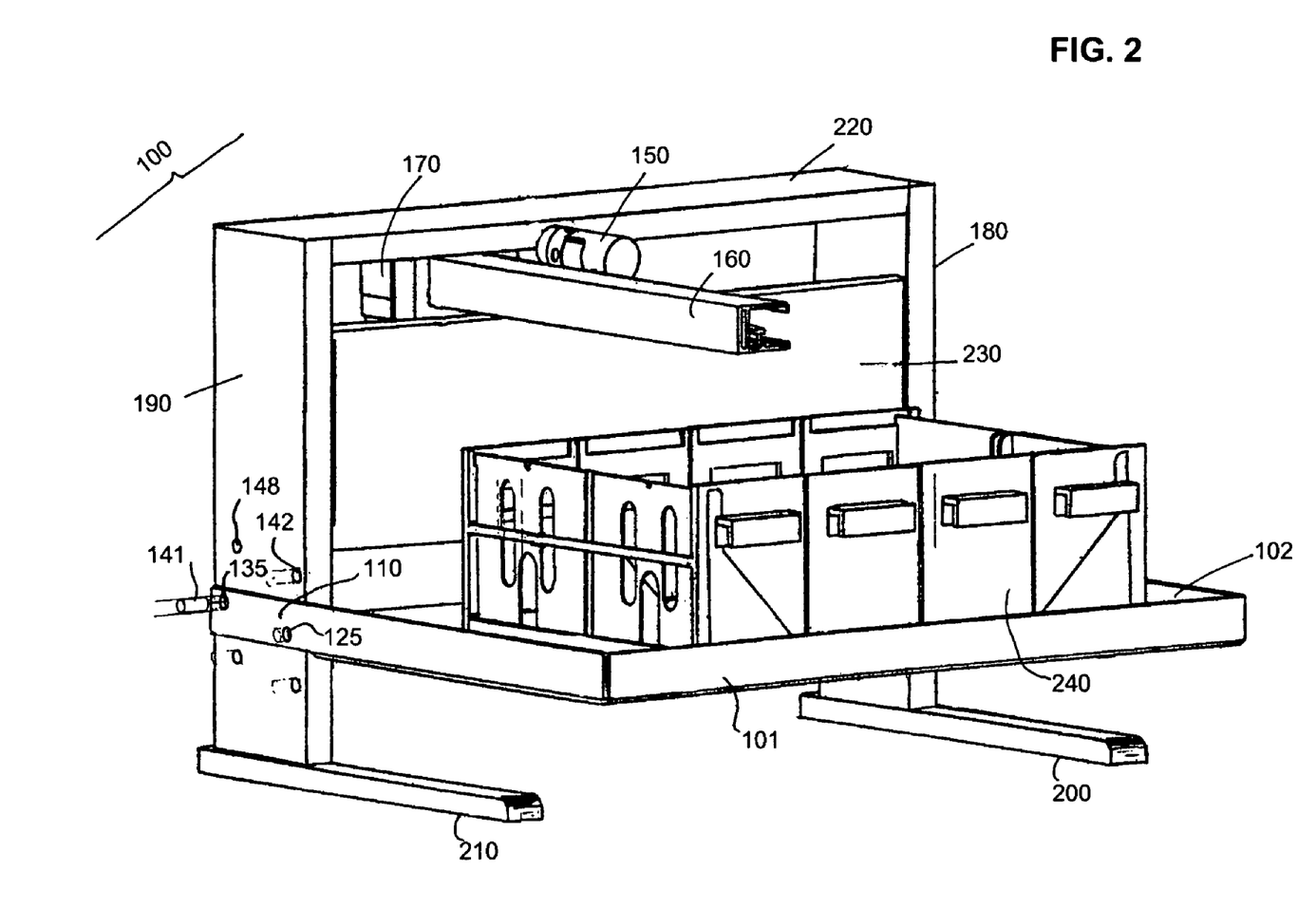
FIG. 2 is a perspective view of a fraction collector demonstrating the use of peg holes in the legs of the fraction collector.
Figure 3:
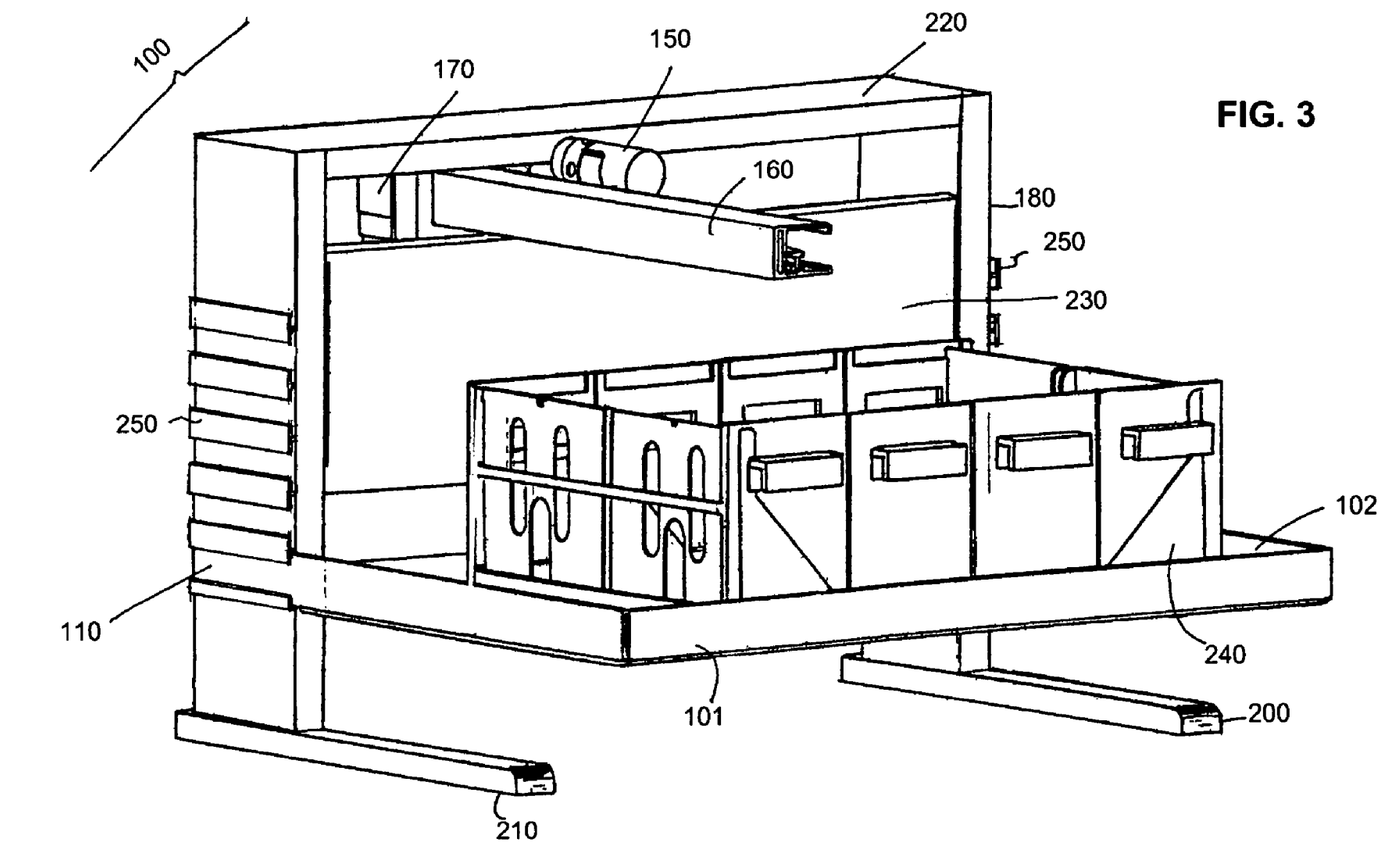
FIG. 3 is a perspective view of a fraction collector demonstrating the use of exterior channels in the legs of a fraction collector.

A number of specific devices for attaching the collection bed are contemplated as demonstrated by FIGS. 1, 2, and 3. In FIG. 1, both the left leg 180 and the right leg 190 have a series of front pegs 140 and rear pegs 145. As shown, all of the pegs are in fixed positions, however the skilled artisan will appreciate that the pegs may also be moveable. FIG. 1 shows the collection bed arms as having front anchoring points 120 and rear anchoring points 130. The collection bed 101 is attached to the left leg 180 and right leg 190 by engaging the front anchoring points 120 with the front pegs 140 and the rear anchoring points 130 with the rear pegs 145. The front pegs 140 and the rear pegs 145 are situated on the left leg 180 and right leg 190 such that the collection bed 101 is level when all the anchoring points are engaged by the corresponding pegs.

In the embodiment of FIG. 1, vertical adjustment of the collection bed 101 is made by manually disengaging the anchoring points 120, 130 and moving the collection bed up or down, depending on the desired location, and then reengaging the anchoring points 120, 130 with the pegs 140, 145 at the new location.

The embodiment of FIG. 2 demonstrates another way of attaching the collection bed 101 to the legs 180, 190 of the fraction collector 100. FIG. 2 shows the collection bed arm 110 as having front 125 and rear 135 anchoring holes, while the left leg 180 and right leg 190 have front 142 and rear 148 peg holes. The peg holes and anchoring holes are positioned such that the front anchoring holes 125 will align with the front peg holes 142 and the rear anchoring holes 135 will align with the rear peg holes 148 when the collection bed 101 is level. When the anchoring holes and peg holes are aligned, movable pegs 141 may be inserted to fix the collection bed 101 to the legs. Although the embodiment demonstrates peg holes and pegs cylindrical in shape, one skilled in the art will understand that the pegs may be any shape, including squares, rectangles, semi-circles and the like. In alternative embodiments, pins will be placed through the anchoring holes and peg holes to fix the collection bed 101 to the legs.

FIG. 3 demonstrates yet another embodiment of the present invention. In FIG. 3, left leg 180 and right leg 190 of the fraction collector have mounted exterior channels 250. In certain embodiments, the exterior channels 250 will not be mounted, but will be an integral part of the legs. In the embodiment of FIG. 3, the collection bed arms 110 are inserted into the exterior channels 250 in order to hold the collection bed in a fixed position. The exterior channels 250 are positioned on the legs, at various heights, such that the collection bed 101 will be level when attached to the fraction collector 100. Numerous channel sizes and spacings may be envisioned by one of ordinary skill in the art in order to achieve a greater or lesser range of height adjustment for the collection bed 101. For example, the exterior channels 250 may be arranged according to collection vessels currently known to exist in the art. It is not an object of this invention to be limited by the illustrated scale of the positions or number of positions shown in the figures.

Figure 4:
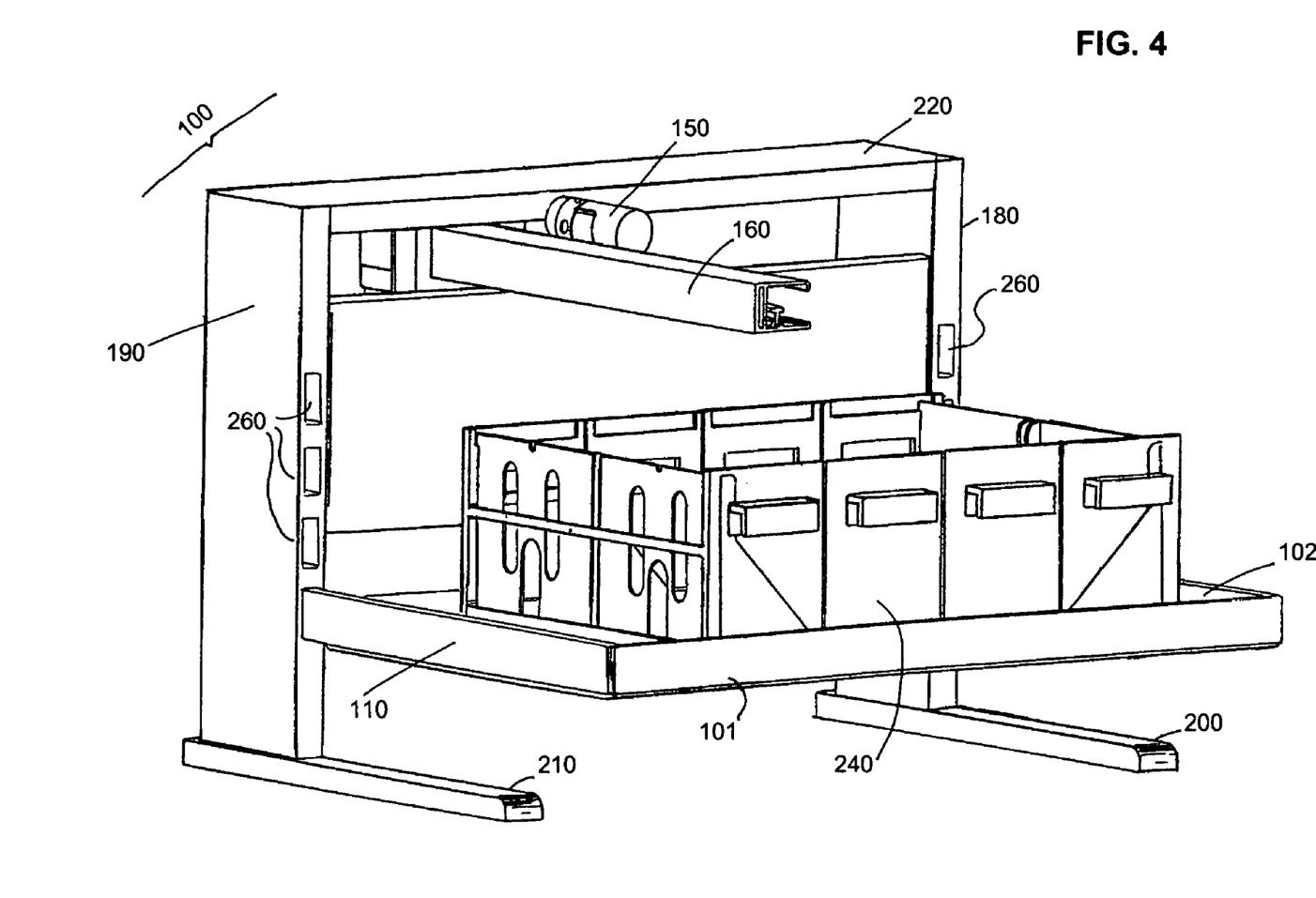
FIG. 4 a perspective view of a fraction collector demonstrating the use of interior channels in the legs of a fraction collector.

The embodiment of FIG. 4 shows an arrangement similar to that in FIG. 3. FIG. 4 demonstrates interior channels 260 recessed into the left and right legs 180, 190 of the fraction collector 100. In this case, the collection bed arms 110 are inserted into the interior channels 260. The interior channels 260 are positioned on the legs, at various heights, such that the collection bed 101 will be level when attached to the fraction collector 100. Once again, the positioning of the interior channels are not meant to be limiting. Furthermore, the skilled artisan will understand that although the exterior channels demonstrated in FIG. 3 and the interior channels demonstrated in FIG. 4 are shown on perpendicular sides of the legs, the channels may be on any side of the leg, as long as the collection bed arms are adapted. In some embodiments, the interior channel will extend through the leg. In other embodiments, the interior channels may be on a parallel side of the leg. If the interior channels are on a parallel side of the leg, the collection bed arm will need to include at least one projection for connection.

Although FIGS. 1-3 demonstrate attachment of the collection bed arm 110 on the outside side of the leg, it is also contemplated that the locus of attachment using any of the above-mentioned attachment devices could be also on the inward facing portion of the legs. Moreover, one of skill in the art will understand that different styles of legs may be used in place of legs 180, 190. In certain embodiments, the legs may encompass legs with grooves, as well as legs having other styles. In some embodiments, both edges of the leg will have cutouts or other types of notches. In other embodiments, only one side of the leg will have grooves or notches. The skilled artisan will understand that the number, size and side of the attachment devices are not meant to be limited by the illustrated scale of the positions or number of positions shown in the figures.

Figure 5:
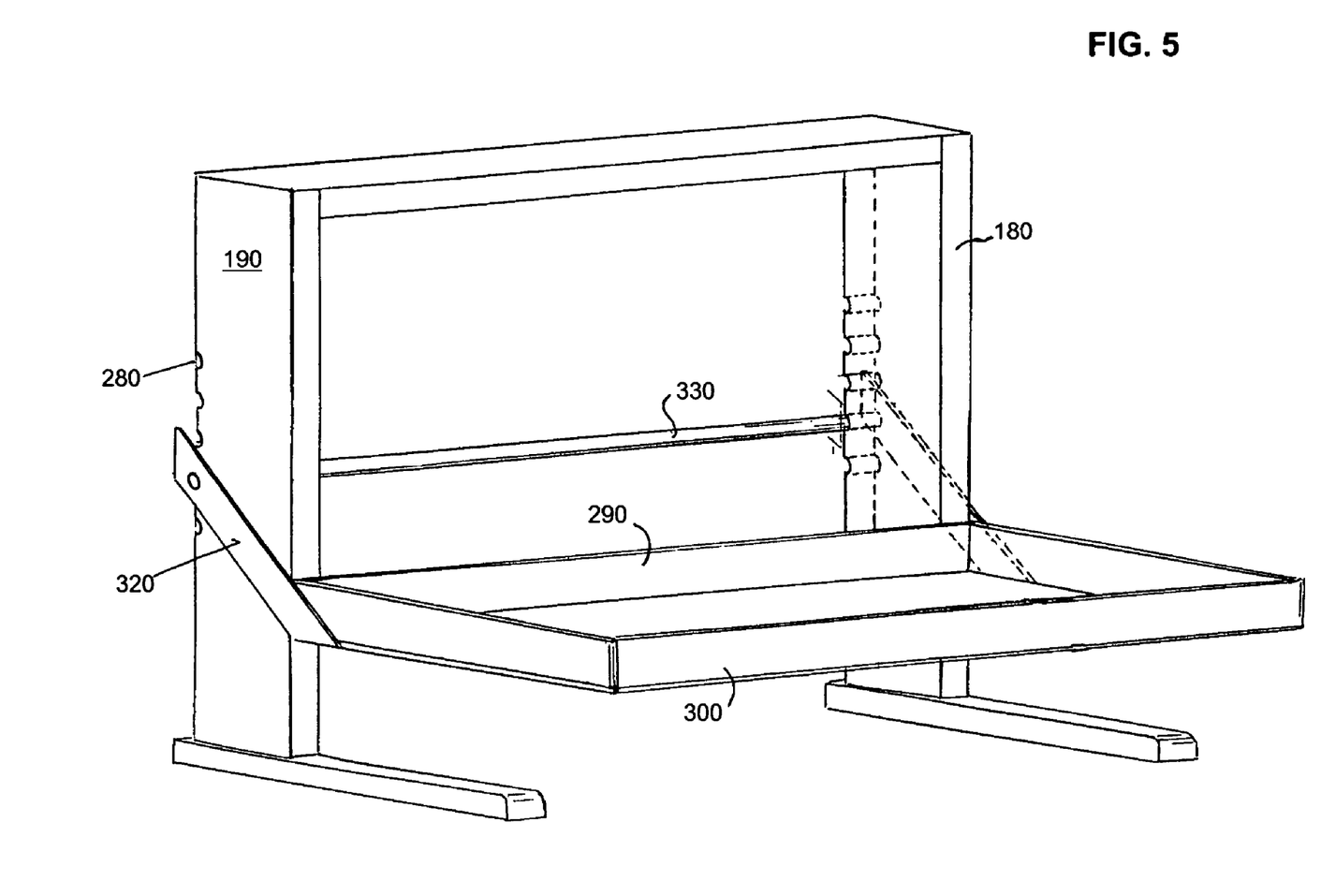
FIG. 5 is a perspective view of an alternative style collection bed.

FIG. 5 shows an embodiment of an alternate style of collection bed assembly 300. In the embodiment of FIG. 5, the leg of the support system includes grooves or notches 280, that are able to receive a rod 330. A rear edge 290 of the collection bed 300 may rest against legs 180, 190 possibly in grooves or notches to further support the collection bed 101. As in FIG. 5, the collection bed arms 320 are angularly disposed from the plane of the collection bed. The arms 320 can either be attached by the rod 330 as shown in FIG. 5, looped, or a rod may only partially extend from one leg to the other. As one of skill in the art understands the extension of the rod may vary in alternative embodiments. The rod can either be short or long while still keeping within the spirit of the invention.

In the embodiment of FIG. 5, the alternate style collection bed 300 is vertically adjusted by raising the front portion of bed 300 enough to free the rear edge 290 from the legs 180, 190 and to release the rod 330 from the grooves 280 and then sliding the collection bed 300 up and down the legs to the desired position. In addition to the grooves 280 as shown in FIG. 5, other embodiments are envisioned. For example, a series of notches that receive a complementarily shaped portion of the rear edge of the collection bed tray is contemplated. Furthermore, the notches could also be locks designed to accept a complementarily shaped key.

Figure 6:
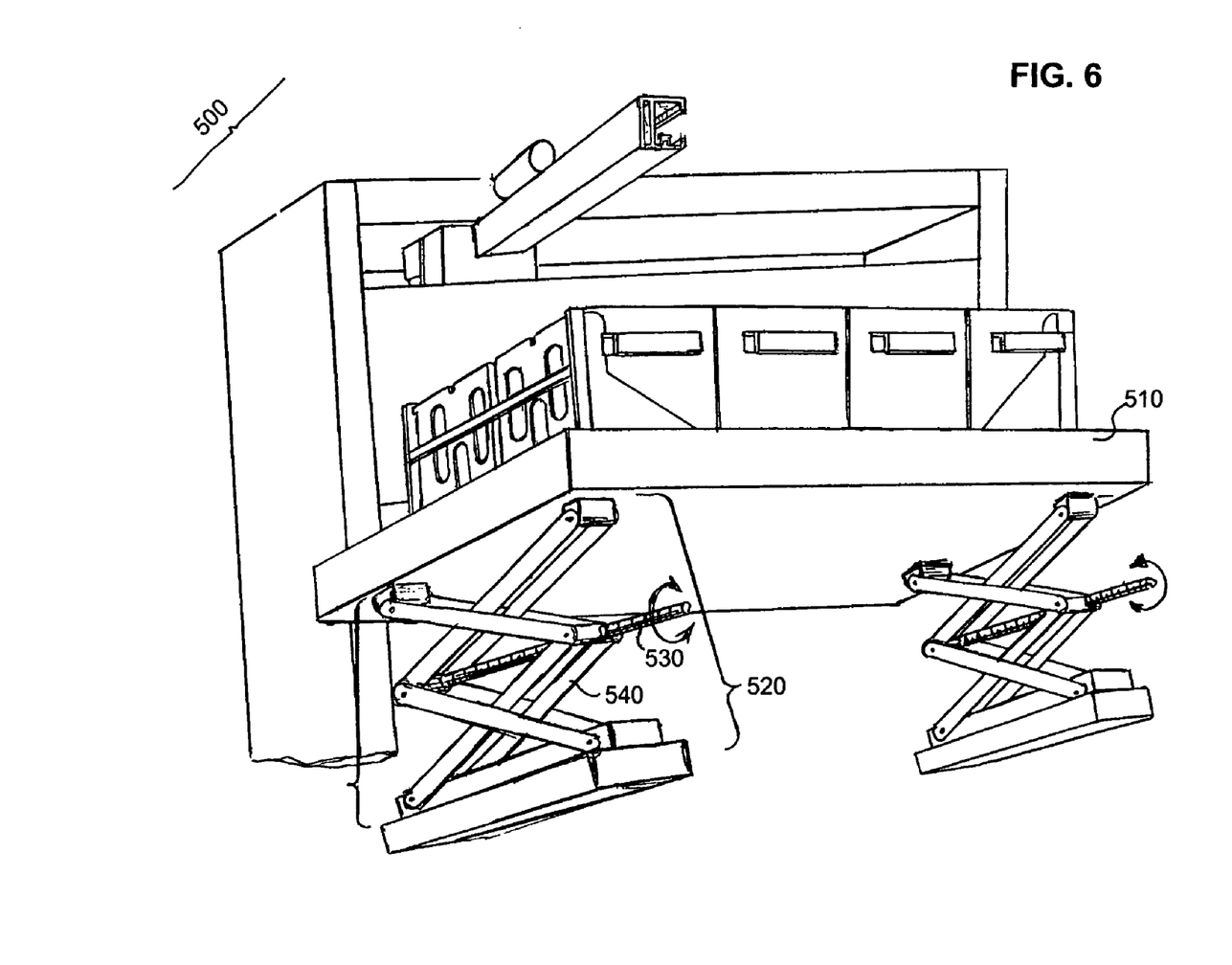
FIG. 6 is a perspective view of a mechanized style collection bed.

Mechanized embodiments of the invention are contemplated. For example, the fraction collector may include a collection bed with a hydraulic lift. As demonstrated by FIG. 6, the fraction collector 500 may comprise a collection bed 510 with a screw-driven lift 520. The screw-driven lift 520 may include a screw 530 and an expandable lattice 540. Although the embodiment shown in FIG. 6 demonstrates two screw driven lifts, the skilled artisan will understand that any number of lifts, as long as they can function with a fraction collector, may be used. It is contemplated that embodiments comprising a hydraulic lift or a screw-driven lift may be motorized with either an automatically driven system or a manually driven system. In the mechanized embodiments, the collection bed may not be attached to the fraction collector. Instead, the collection bed may rest upon or fully integrate with a stage that can be raised or lowered manually, via hydraulic methods, or with a motorized screw mechanism. In such embodiments, the collection bed needs to be reliably and precisely aligned with the dispensing head on the apparatus. Precise alignment could be carried out via markings on the apparatus and collection bed, positioning lasers on the apparatus, and/or with markings on both the apparatus and support on which the apparatus rests, such as a bench. Because mechanized versions add a layer of complexity to the vertically adjustable collection bed, and may be impractical in certain situations and because mechanized versions utilize mechanics well understood by the skilled artisan, these embodiments will not be further described.

While embodiments of the foregoing invention have been described in some detail and by way of illustration and example to provide clarity and understanding, it should be understood that certain changes and modifications can be made therein in accordance with ordinary skill in the art without departing from the invention in its broader aspects as defined in the following claims.

What is claimed is:

1. A fraction collector, comprising:
   a support system;
   a carriage moveably supported by the support system;
   an extension arm connected to the carriage;
   a dispensing head moveably connected to the extension arm; wherein the dispensing head and carriage can move relative to the support system in a first plane; and
   a collection bed moveably connected to the support system wherein the collection bed can be moved in a second plane perpendicular to the first plane without moving the support system.

2. The fraction collector of claim 1 wherein the support system further comprises a front brace.

3. The fraction collector of claim 1 wherein the tray area is designed to support at least one rack, wherein the at least one rack is designed to hold at least one collection vessel.

4. The fraction collector of claim 1 wherein the left leg comprises a first peg, the right leg comprises a second peg and the collection bed arms each comprise an anchor point designed to receive the first peg or the second peg.

5. The fraction collector of claim 4 wherein the anchor point is a slot.

6. The fraction collector of claim 4 wherein the anchor point is a hole.

7. The fraction collector of claim 4 wherein the first peg and the second peg are fixed.

8. The fraction collector of claim 1 wherein the left leg comprises a first hole, the right leg comprises a second hole, and the collection bed arms each comprise an anchor point, and further wherein the first hole, the second hole, and the anchor points are designed to receive a peg.

9. The fraction collector of claim 1 wherein the right leg and the left leg include exterior channels, and further wherein the collection bed arms are insertable into the exterior channels.

10. The fraction collector of claim 1 wherein the right leg and the left leg include interior channels, and further wherein the collection bed arms are insertable into the interior channels.

11. The fraction collector of claim 1 further comprising a rod, wherein the collection bed arms include a hole capable of receiving an end of the rod, and further wherein the first leg and the right leg include grooves capable of supporting the rod along an edge opposite the collection bed.

12. The fraction collector of claim 11 wherein the collection bed arms are angularly disposed relative to the tray area.

13. The fraction collector of claim 11 wherein the right leg and the left leg further comprise a groove for supporting the collection bed.

14. The fraction collector of claim 13 wherein the collection bed comprises a rear edge, and further wherein the rear edge comprises a complementary shape to fit the groove.

* * * * *